United States Patent [19]

Yokoyama et al.

[11] Patent Number: 6,046,346
[45] Date of Patent: Apr. 4, 2000

[54] PRODUCTION OF ALKALI METAL CYCLOPENTADIENYLIDE AND PRODUCTION OF DIHALOBIS (η-SUBSTITUTED-CYCLOPENTADIENYL) ZIRCONIUM FROM ALKALI METAL CYCLOPENTADIENYLIDE

[75] Inventors: Keiichi Yokoyama; Kenji Sugiyama; Akira Yoshikawa, all of Wakayama, Japan

[73] Assignee: Honshu Chemical Industry Co., Ltd., Tokyo, Japan

[21] Appl. No.: 09/209,752

[22] Filed: Dec. 11, 1998

[30] Foreign Application Priority Data

Dec. 26, 1997 [JP] Japan .................................. 9-359460

[51] Int. Cl.$^7$ .............................. C07F 17/00; C07F 7/00
[52] U.S. Cl. ......................... 556/53; 589/350; 589/380; 526/160; 526/943; 987/2; 502/103; 502/117
[58] Field of Search ............................... 556/53; 585/350, 585/380; 987/2; 526/160, 943; 562/103, 117

[56] References Cited

U.S. PATENT DOCUMENTS 4,874,880  10/1989  Miya et al. ................................ 556/53
5,585,509  12/1996  Langhauser et al. .................... 556/11

OTHER PUBLICATIONS

Patent Abstracts of Japan —Publication No. 63222177A publication date Sep. 16, 1988.
Organic Synthesis, Collective vol. 5, pp. 1088–1091.
"Solution Structure and Dynamics of Binuclear Dinitrogen . . ." Journal of the American Chemical Society, 100, May 10, 1978 pp. 3078–3083.
"Cyclopentadienyl Metal Carbonyls and Some Derivatives", Inorganic Synthesis vol. 7 (1963) pp. 99–103.

*Primary Examiner*—Porfirio Nazario-Gonzalez
*Attorney, Agent, or Firm*—Birch, Stewart, Kolasch & Birch, LLP

[57] ABSTRACT

A process for producing an alkali metal cyclopentadienylide is disclosed which comprises reacting in a solvent an alkali metal hydride with a disubstituted or trisubstituted 1,3-cyclopentadiene. Further, a process for producing a dihalobis(η-substituted-cyclopentadienyl)zirconium is disclosed which comprises reacting a zirconium halide with the above alkali metal cyclopentadienylide. The former process enables performing the reaction between the disubstituted or trisubstituted 1,3-cyclopentadiene and the alkali metal hydride at an easily controllable temperature of room temperature to about 150° C. and also enables obtaining the alkali metal cyclopentadienylide in high yield. The latter process enables obtaining the dihalobis(η-substituted-cyclopentadienyl)zirconium in high yield.

11 Claims, No Drawings

PRODUCTION OF ALKALI METAL CYCLOPENTADIENYLIDE AND PRODUCTION OF DIHALOBIS (η-SUBSTITUTED-CYCLOPENTADIENYL) ZIRCONIUM FROM ALKALI METAL CYCLOPENTADIENYLIDE

FIELD OF THE INVENTION

The present invention relates to a process for producing an alkali metal cyclopentadienylide which is an alkali metal salt of a disubstituted or trisubstituted cyclopentadienyl anion and relates to a process for producing a dihalobis(η-substituted-cyclopentadienyl)zirconium from the alkali metal cyclopentadienylide obtained by the above process. The alkali metal cyclopentadienylide is useful as a cyclopentadienyl group introducing agent and a metallocene synthetic agent. The dihalobis(η-substituted-cyclopentadienyl)zirconium is useful as an olefin polymerization catalyst, an acetylene carbometallizing agent, a starting material for the synthesis of a monohydride homologue and a vulcanizing agent for a silicone material and a rubber.

BACKGROUND OF THE INVENTION

It is known that unsubstituted 1,3-cyclopentadiene reacts with a metallic sodium to produce a sodium salt of cyclopentadienyl anion (sodium cyclopentadienylide) (see K. Hafner and H. Kaiser, Org. Syn. Coll., vol. 5, 1088 (1973) and R. B. King and F. G. A. Stone, Inorg. Syn. 7, 99 (1963)).

Further, it is known that a disubstituted 1,3-cyclopentadiene reacts with butyllithium (BuLi) to produce a lithium salt of cyclopentadienyl anion (disubstituted lithium cyclopentadienylide) (see Japanese Patent Laid-open Publication No. 63(1988)-222177).

Still further, it is known that a pentasubstituted 1,3-cyclopentadiene reacts with BuLi to produce a lithium salt of cyclopentadienyl anion (pentasubstituted lithium cyclopentadienylide) (see JACS, 100, 3078 (1978)).

Conventionally, the anionization of a disubstituted or trisubstituted cyclopentadiene is performed by the reaction with an alkyllithium such as butyllithium (BuLi), and no other method has been known. This anionization of a disubstituted or trisubstituted cyclopentadiene by the reaction with an alkyllithium must be carried out at low temperatures such as −78 to 0° C., so that the temperature control is not easy. Further, the alkyllithium is expensive and is difficult to handle in the air. Still further, there are disadvantages such that the upper limit of the concentration of butyllithium which is available in the market is as low as 2 mol/lit., so that desirably high efficiency of a reaction vessel cannot be attained.

Therefore, the inventors have made extensive and intensive studies with a view toward solving the above problem. As a result, it has been found that sodium hydride (NaH) which is inexpensive and is easy to handle in the air reacts with a disubstituted or trisubstituted cyclopentadiene at room temperature to about 150° C. so that the disubstituted or trisubstituted cyclopentadiene are anionized to enable obtaining sodium cyclopentadienylides with high yield, generally at least 85%. The present invention has been completed on the basis of this finding.

OBJECT OF THE INVENTION

The present invention has been made with a view toward overcoming the above drawbacks of the prior art. Accordingly, an object of the present invention is to provide a process for producing an alkali metal cyclopentadienylide, in which a disubstituted or trisubstituted alkali metal cyclopentadienylide can be obtained with high yield by anionizing a disubstituted or trisubstituted cyclopentadiene.

Another object of the present invention is to provide a process for producing a dihalobis(η-substituted-cyclopentadienyl)zirconium, in which use is made of the alkali metal cyclopentadienylide obtained by the above process.

SUMMARY OF THE INVENTION

The process for producing an alkali metal cyclopentadienylide according to the present invention comprises reacting in a solvent an alkali metal hydride with a disubstituted or trisubstituted 1,3-cyclopentadiene represented by the general formula:

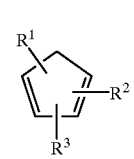

[I]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms; and $R^3$ is a hydrogen atom or an alkyl group having 1 to 3 carbon atoms, thereby obtaining an alkali metal cyclopentadienylide represented by the general formula:

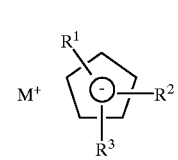

[II]

wherein $R^1$, $R^2$ and $R^3$ are as defined above with respect to the general formula [I]; and $M^+$ is an alkali metal ion.

In the present invention, preferred use is made of the following process (1) or (2) in which an ether solvent is used in the above reaction.

The process (1) comprises reacting in an ether solvent an alkali metal hydride with a disubstituted 1,3-cyclopentadiene represented by the general formula:

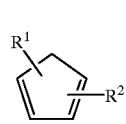

[I-a]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms, thereby obtaining an alkali metal cyclopentadienylide represented by the general formula:

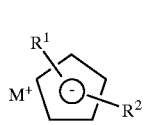

[II-a]

wherein $R^1$ and $R^2$ are as defined above with respect to the general formula [I-a]; and $M^+$ is an alkali metal ion.

It is preferred that the disubstituted 1,3-cyclopentadiene be a 1,3-cyclopentadiene having alkyl substituents at its 1- and 3-positions. It is especially preferred that the disubstituted 1,3-cyclopentadiene be a disubstituted 1,3-cyclopentadiene having a methyl group at its 3-position, represented by the formula:

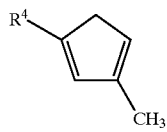

wherein $R^4$ is an alkyl group having 1 to 8 carbon atoms, an aryl group having 6 to 10 carbon atoms or an aralkyl group having 7 to 9 carbon atoms.

On the other hand, the process (2) comprises reacting in an ether solvent an alkali metal hydride with a trisubstituted 1,3-cyclopentadiene represented by the general formula:

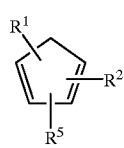

[I-b]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms; and $R^5$ is an alkyl group having 1 to 3 carbon atoms, thereby obtaining an alkali metal cyclopentadienylide represented by the general formula:

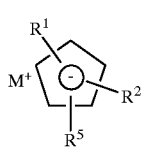

[II-b]

wherein $R^1$, $R^2$ and $R^5$ are as defined above with respect to the general formula [I-b]; and $M^+$ is an alkali metal ion.

Of the compounds represented by the above general formula [II-a], a novel compound according to the present invention is a sodium salt compound of a 1,3-disubstituted cyclopentadienyl anion represented by the following general formula [II-c]:

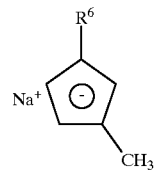

[II-c]

wherein $R^6$ is an alkyl group having 1 to 6 carbon atoms.

The process for producing a dihalobis(η-substituted-cyclopentadienyl)zirconium according to the present invention comprises reacting a zirconium halide with the alkali metal cyclopentadienylide produced by the above process of the present invention, thereby obtaining a dichlorobis(η-substituted-cyclopentadienyl)zirconium represented by the general formula:

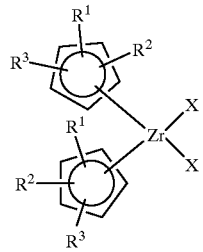

[III]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms;

$R^3$ is a hydrogen atom or an alkyl group having 1 to 3 carbon atoms; and

X is a halogen atom.

DETAILED DESCRIPTION OF THE INVENTION

The process for producing an alkali metal cyclopentadienylide according to the present invention and the process for producing a dihalobis(η-substituted-cyclopentadienyl) zirconium from the alkali metal cyclopentadienylide obtained by the above process according to the present invention will be described in detail below.

In the process for producing an alkali metal cyclopentadienylide according to the present invention, an alkali metal hydride is reacted with a disubstituted or trisubstituted 1,3-cyclopentadiene in a solvent.

1,3-Cyclopentadiene

The disubstituted or trisubstituted 1,3-cyclopentadiene for use in the present invention is represented by the following general formula [I]. The general formula [I] can be particularized into the general formula [I-a] representing disubstituted 1,3-cyclopentadienes and the general formula [I-b] representing trisubstituted 1,3-cyclopentadienes.

In the general formula:

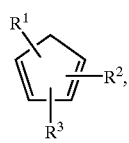

each of R¹ and R² is independently an alkyl group having 1 to 8 carbon atoms, an aryl group having 6 to 10 carbon atoms, an alkenyl group having 2 to 8 carbon atoms or an aralkyl group having 7 to 9 carbon atoms; and R³ is a hydrogen atom or an alkyl group having 1 to 3 carbon atoms.

The alkyl group having 1 to 8 carbon atoms for R¹ or R² is, for example, a methyl group, an ethyl group, a n-propyl group, an isopropyl group, a n-butyl group, an isobutyl group, a t-butyl group, a n-pentyl group, an isopentyl group, a neopentyl group, a n-hexyl group, an isohexyl group, a n-heptyl group, a n-octyl group, a sec-butyl group, a sec-amyl group or a sec-pentyl group.

The aryl group having 6 to 10 carbon atoms for R¹ or R² is, for example, a phenyl group, a tolyl group, a naphthyl group, a xylyl group, a mesityl group, an ethylphenyl group, a propylphenyl group, a butylphenyl group or a diethylphenyl group.

The alkenyl group having 2 to 8 carbon atoms for R¹ or R² is, for example, a vinyl group, a 1-propenyl group, a 2-propenyl group (allyl group), an isopropenyl group, a 1-butenyl group, a 2-butenyl group, an isobutenyl group, a 3-hexenyl group, a 1-pentenyl group, a 2-pentenyl group or a 1-hexenyl group.

The aralkyl group having 7 to 9 carbon atoms for R¹ or R² is, for example, a benzyl group, a phenethyl group or a phenylpropyl group.

The alkyl group having 1 to 3 carbon atoms, represented by R³, is, for example, a methyl group, an ethyl group, a n-propyl group or an isopropyl group.

In the general formula:

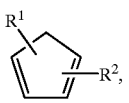

R¹ and R² are as defined above with respect to the general formula [I].

It is preferred that the above disubstituted 1,3-cyclopentadiene be a 1,3-cyclopentadiene having alkyl substituents at its 1- and 3-positions. It is especially preferred that the disubstituted 1,3-cyclopentadiene be a disubstituted 1,3-cyclopentadiene having a methyl group at its 3-position, represented by the formula:

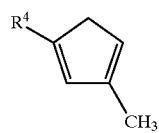

wherein R⁴ is an alkyl group having 1 to 8 carbon atoms, an aryl group having 6 to 10 carbon atoms or an aralkyl group having 7 to 9 carbon atoms.

The alkyl group having 1 to 8 carbon atoms for R⁴ is, for example, a methyl group, an ethyl group, a n-propyl group, an isopropyl group, a n-butyl group, an isobutyl group, a t-butyl group, a n-pentyl group, an isopentyl group, a neopentyl group, a n-hexyl group, an isohexyl group, a n-heptyl group, a n-octyl group, a sec-butyl group, a sec-amyl group or a sec-pentyl group. Of these, preferred is an alkyl group having 1 to 6 carbon atoms and especially preferred is an alkyl group having 1 to 4 carbon atoms.

The aryl group having 6 to 10 carbon atoms for R⁴ is, for example, a phenyl group, a tolyl group, a naphthyl group, a xylyl group, a mesityl group, an ethylphenyl group, a propylphenyl group, a butylphenyl group or a diethylphenyl group.

The aralkyl group having 7 to 9 carbon atoms for R⁴ is, for example, a benzyl group, a phenethyl group or a phenylpropyl group.

In the general formula:

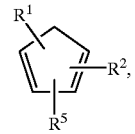

R¹ and R² are as defined above with respect to the general formula [I]; and R⁵ is an alkyl group having 1 to 3 carbon atoms. Examples of R⁵ include those mentioned for R³ in the general formula [I].

Examples of the disubstituted 1,3-cyclopentadienes represented by the general formula [I-a] include:
dialkyl-substituted 1,3-cyclopentadienes such as
1,3-dimethyl-1,3-cyclopentadiene,
1,4-dimethyl-1,3-cyclopentadiene,
2,5-dimethyl-1,3-cyclopentadiene,
1-methyl-3-ethyl-1,3-cyclopentadiene,
1-methyl-4-ethyl-1,3-cyclopentadiene,
1-methyl-3-n-propyl-1,3-cyclopentadiene,
1-methyl-4-n-propyl-1,3-cyclopentadiene,
1-methyl-3-isopropyl-1,3-cyclopentadiene,
1-methyl-3-n-butyl-1,3-cyclopentadiene,
1-methyl-3-isobutyl-1,3-cyclopentadiene,
1-methyl-3-t-butyl-1,3-cyclopentadiene,
1-methyl-4-n-butyl-1,3-cyclopentadiene,
1-methyl-3-n-butyl-1,3-cyclopentadiene,
2-methyl-5-n-butyl-1,3-cyclopentadiene,
1-methyl-3-n-pentyl-1,3-cyclopentadiene,
1-methyl-3-n-hexyl-1,3-cyclopentadiene,
1-methyl-3-n-octyl-1,3-cyclopentadiene,
1-methyl-3-n-decyl-1,3-cyclopentadiene,
1,3-diethyl-1,3-cyclopentadiene,
1-ethyl-3-methyl-1,3-cyclopentadiene,
1-ethyl-3-n-propyl-1,3-cyclopentadiene,
1-ethyl-3-n-butyl-1,3-cyclopentadiene,
1-ethyl-3-n-octyl-1,3-cyclopentadiene,
1-ethyl-3-n-decyl-1,3-cyclopentadiene,
1,3-di-n-propyl-1,3-cyclopentadiene,
1,3-diisopropyl-1,3-cyclopentadiene,
1-n-propyl-3-methyl-1,3-cyclopentadiene,
1-n-propyl-3-n-butyl-1,3-cyclopentadiene,
1-isopropyl-3-methyl-1,3-cyclopentadiene,
1-isopropyl-3-n-butyl-1,3-cyclopentadiene,
1-n-propyl-3-methyl-1,3-cyclopentadiene,
1-n-propyl-3-isobutyl-1,3-cyclopentadiene, and
1-n-propyl-3-t-butyl-1,3-cyclopentadiene;
alkyl/aralkyl-substituted 1,3-cyclopentadienes such as
1-methyl-3-benzyl-1,3-cyclopentadiene,
1-ethyl-3-benzyl-1,3-cyclopentadiene, 1-n-propyl-3-benzyl-1,3-cyclopentadiene,
1-isopropyl-3-benzyl-1,3-cyclopentadiene,
1-n-butyl-3-benzyl-1,3-cyclopentadiene,
1-isobutyl-3-benzyl-1,3-cyclopentadiene,
1-t-butyl-3-benzyl-1,3-cyclopentadiene,
1-benzyl-3-methyl-1,3-cyclopentadiene,
1-methyl-3-phenethyl-1,3-cyclopentadiene,
1-ethyl-3-phenethyl-1,3-cyclopentadiene,
1-n-propyl-3-phenethyl-1,3-cyclopentadiene,
1-isopropyl-3-phenethyl-1,3-cyclopentadiene,
1-n-butyl-3-phenethyl-1,3-cyclopentadiene,
1-isobutyl-3-phenethyl-1,3-cyclopentadiene,
1-t-butyl-3-phenethyl-1,3-cyclopentadiene, and
1-phenethyl-3-methyl-1,3-cyclopentadiene;
alkyl/aryl-substituted 1,3-cyclopentadienes such as
1-methyl-3-phenyl-1,3-cyclopentadiene,
1-ethyl-3-phenyl-1,3-cyclopentadiene,
1-n-propyl-3-phenyl-1,3-cyclopentadiene,
1-isopropyl-3-phenyl-1,3-cyclopentadiene,
1-n-butyl-3-phenyl-1,3-cyclopentadiene,
1-isobutyl-3-phenyl-1,3-cyclopentadiene,
1-t-butyl-3-phenyl-1,3-cyclopentadiene, and
1-phenyl-3-methyl-1,3-cyclopentadiene; and
alkyl/alkenyl-substituted 1,3-cyclopentadienes such as
1-methyl-3-vinyl-1,3-cyclopentadiene,
1-methyl-3-1-propenyl-1,3-cyclopentadiene,
1-methyl-3-isopropenyl-1,3-cyclopentadiene,
1-methyl-3-allyl-1,3-cyclopentadiene,
1-methyl-3-2-butenyl-1,3-cyclopentadiene,
1-methyl-3-isobutenyl-1,3-cyclopentadiene,
1-methyl-3-2-pentenyl-1,3-cyclopentadiene,
1-methyl-3-3-hexenyl-1,3-cyclopentadiene,
1-ethyl-3-vinyl-1,3-cyclopentadiene,
1-ethyl-3-1-propenyl-1,3-cyclopentadiene,
1-ethyl-3-isopropenyl-1,3-cyclopentadiene,
1-ethyl-3-allyl-1,3-cyclopentadiene,
1-ethyl-3-2-butenyl-1,3-cyclopentadiene,
1-ethyl-3-isobutenyl-1,3-cyclopentadiene,
1-ethyl-3-2-pentenyl-1,3-cyclopentadiene,
1-ethyl-3-3-hexenyl-1,3-cyclopentadiene,
1-vinyl-3-methyl-1,3-cyclopentadiene,
1-1-propenyl-3-methyl-1,3-cyclopentadiene,
1-isopropenyl-3-methyl-1,3-cyclopentadiene,
1-allyl-3-methyl-1,3-cyclopentadiene,
1-2-butenyl-3-methyl-1,3-cyclopentadiene,
1-isobutenyl-3-methyl-1,3-cyclopentadiene,
1-2-pentenyl-3-methyl-1,3-cyclopentadiene, and
1-3-hexenyl-3-methyl-1,3-cyclopentadiene.

Examples of the trisubstituted 1,3-cyclopentadienes represented by the general formula [I-b] include:
trialkyl-substituted 1,3-cyclopentadienes such as
1,3-dimethyl-4-ethyl-1,3-cyclopentadiene,
1,3-dimethyl-4-n-propyl-1,3-cyclopentadiene,
1,3-dimethyl-4-isopropyl-1,3-cyclopentadiene,
1,3-dimethyl-4-n-butyl-1,3-cyclopentadiene,
1,3-dimethyl-4-isobutyl-1,3-cyclopentadiene,
1,3-dimethyl-4-t-butyl-1,3-cyclopentadiene,
1,3-dimethyl-4-n-hexyl-1,3-cyclopentadiene,
1,4-dimethyl-3-ethyl-1,3-cyclopentadiene,
1,4-dimethyl-3-n-propyl-1,3-cyclopentadiene,
1,4-dimethyl-3-isopropyl-1,3-cyclopentadiene,
1,4-dimethyl-3-n-butyl-1,3-cyclopentadiene,
1,4-dimethyl-3-isobutyl-1,3-cyclopentadiene,
1,4-dimethyl-3-t-butyl-1,3-cyclopentadiene,
1,4-dimethyl-3-n-hexyl-1,3-cyclopentadiene,
1,5-dimethyl-3-ethyl-1,3-cyclopentadiene,
1,5-dimethyl-3-n-propyl-1,3-cyclopentadiene,
1,5-dimethyl-3-isopropyl-1,3-cyclopentadiene,
1,5-dimethyl-3-n-butyl-1,3-cyclopentadiene,
1,5-dimethyl-3-isobutyl-1,3-cyclopentadiene,
1,5-dimethyl-3-t-butyl-1,3-cyclopentadiene, and
1,5-dimethyl-3-n-hexyl-1,3-cyclopentadiene;
dialkyl/aralkyl-substituted 1,3-cyclopentadienes such as
1,4-dimethyl-3-benzyl-1,3-cyclopentadiene,
1-methyl-4-ethyl-3-benzyl-1,3-cyclopentadiene,
1-methyl-4-n-propyl-3-benzyl-1,3-cyclopentadiene,
1-methyl-4-isopropyl-3-benzyl-1,3-cyclopentadiene,
1-methyl-4-n-butyl-3-benzyl-1,3-cyclopentadiene,
1-methyl-4-isobutyl-3-benzyl-1,3-cyclopentadiene,
1-methyl-4-t-butyl-3-benzyl-1,3-cyclopentadiene,
1,4-diethyl-3-benzyl-1,3-cyclopentadiene,
1-ethyl-4-methyl-3-benzyl-1,3-cyclopentadiene,
1-ethyl-4-n-propyl-3-benzyl-1,3-cyclopentadiene,
1-ethyl-4-isopropyl-3-benzyl-1,3-cyclopentadiene,
1-ethyl-4-n-butyl-3-benzyl-1,3-cyclopentadiene,
1-ethyl-4-isobutyl-3-benzyl-1,3-cyclopentadiene,
1-ethyl-4-t-butyl-3-benzyl-1,3-cyclopentadiene,
1,4-di-n-butyl-3-benzyl-1,3-cyclopentadiene,
1,4-dimethyl-3-phenethyl-1,3-cyclopentadiene,
1,4-diethyl-3-phenethyl-1,3-cyclopentadiene,
1,4-di-n-butyl-3-phenethyl-1,3-cyclopentadiene,
1,3-dimethyl-4-benzyl-1,3-cyclopentadiene,
3-methyl-4-ethyl-1-benzyl-1,3-cyclopentadiene,
3-methyl-4-n-propyl-1-benzyl-1,3-cyclopentadiene,
3-methyl-4-isopropyl-1-benzyl-1,3-cyclopentadiene,
3-methyl-4-n-butyl-1-benzyl-1,3-cyclopentadiene,
3-methyl-4-isobutyl-1-benzyl-1,3-cyclopentadiene, and
3-methyl-4-t-butyl-1-benzyl-1,3-cyclopentadiene;
dialkyl/aryl-substituted 1,3-cyclopentadienes such as
1,4-dimethyl-3-phenyl-1,3-cyclopentadiene,
1,4-diethyl-3-phenyl-1,3-cyclopentadiene,
1,4-di-n-butyl-3-phenyl-1,3-cyclopentadiene,
1,4-diisobutyl-3-phenyl-1,3-cyclopentadiene,
1-methyl-4-ethyl-3-phenyl-1,3-cyclopentadiene,
1-ethyl-4-methyl-3-phenyl-1,3-cyclopentadiene,
1-isopropyl-4-methyl-3-phenyl-1,3-cyclopentadiene, and
1-phenyl-4-ethyl-3-methyl-1,3-cyclopentadiene; and
dialkyl/alkenyl-substituted 1,3-cyclopentadienes such as
1,4-dimethyl-3-vinyl-1,3-cyclopentadiene,
1,4-dimethyl-3-1-propenyl-1,3-cyclopentadiene,
1,4-dimethyl-3-isopropenyl-1,3-cyclopentadiene,
1,4-dimethyl-3-allyl-1,3-cyclopentadiene,
1,4-dimethyl-3-2-butenyl-1,3-cyclopentadiene,
1,4-dimethyl-3-isobutenyl-1,3-cyclopentadiene,
1,4-dimethyl-3-2-pentenyl-1,3-cyclopentadiene,
1,4-dimethyl-3-3-hexenyl-1,3-cyclopentadiene,
1,4-diethyl-3-vinyl-1,3-cyclopentadiene,
1,4-diethyl-3-1-propenyl-1,3-cyclopentadiene,
1,4-diethyl-3-isopropenyl-1,3-cyclopentadiene,
1,4-diethyl-3-allyl-1,3-cyclopentadiene,
1,4-diethyl-3-2-butenyl-1,3-cyclopentadiene,
1,4-diethyl-3-isobutenyl-1,3-cyclopentadiene,
1,4-diethyl-3-2-pentenyl-1,3-cyclopentadiene,
1,4-diethyl-3-3-hexenyl-1,3-cyclopentadiene,
1-ethyl-4-methyl-3-vinyl-1,3-cyclopentadiene,
1-ethyl-4-methyl-3-1-propenyl-1,3-cyclopentadiene,
1-ethyl-4-methyl-3-isopropenyl-1,3-cyclopentadiene,
1-ethyl-4-methyl-3-allyl-1,3-cyclopentadiene,
1-ethyl-4-methyl-3-2-butenyl-1,3-cyclopentadiene,
1-ethyl-4-methyl-3-isobutenyl-1,3-cyclopentadiene,
1-ethyl-4-methyl-3-2-pentenyl-1,3-cyclopentadiene,
1-ethyl-4-methyl-3-3-hexenyl-1,3-cyclopentadiene,
1-ethyl-3-methyl-4-vinyl-1,3-cyclopentadiene,
1-ethyl-3-methyl-4-1-propenyl-1,3-cyclopentadiene, 1-ethyl-3-methyl-4-isopropenyl-1,3-cyclopentadiene,
1-ethyl-3-methyl-4-allyl-1,3-cyclopentadiene,
1-ethyl-3-methyl-4-2-butenyl-1,3-cyclopentadiene,
1-ethyl-3-methyl-4-isobutenyl-1,3-cyclopentadiene,
1-ethyl-3-methyl-4-2-pentenyl-1,3-cyclopentadiene, and
1-ethyl-3-methyl-4-3-hexenyl-1,3-cyclopentadiene.

Alkali Metal Hydride

Examples of the alkali metal hydrides for use in the present invention include sodium hydride, potassium hydride and lithium hydride. Of these, sodium hydride and lithium hydride are preferred. Sodium hydride is especially preferred.

In the present invention, the alkali metal hydride can be used in the form of a mixture with a mineral oil as it is or in the form of powder obtained by removing the mineral oil from this mixture with the use of a solvent which is inert to the alkali metal hydride. Sodium hydride is inexpensive and is easy to handle in the air. It is preferred that lithium hydride be handled in a nitrogen atmosphere.

The alkali metal hydride can be used in an amount of 0.9 to 2 mol, preferably, 1.0 to 1.5 mol per mol of the disubstituted or trisubstituted 1,3-cyclopentadiene.

Solvent

Although any solvent can be used in the present invention as long as it is inert in the reaction, preferred is an ether solvent which is inert in the reaction and which has a high dielectric constant. Examples of suitable ether solvents include tetrahydrofuran (THF), 1,3-dioxolane, dimethoxyethane (DME), dioxane, diethyl ether and dibutyl ether.

The ether solvent can generally be used in an amount of 30 to 800 parts by weight, preferably, 40 to 400 parts by weight and, still preferably, 50 to 200 parts by weight based on 100 parts by weight of the disubstituted or trisubstituted 1,3-cyclopentadiene. Of these, particularly preferred are saturated cyclic ether compounds having a 5- or 6-membered ring because they are easy to handle and are also economically excellent.

Reaction Condition

The reaction between the disubstituted or trisubstituted 1,3-cyclopentadiene and the alkali metal hydride can be conducted at room temperature (250°) to about 150° C. preferably, 50 to 100° C. for a period of, generally, 1 to 48 hr, preferably, 5 to 26 hr. The reaction is preferably conducted in an atmosphere of inert gas such as nitrogen gas.

When the reaction between the disubstituted or trisubstituted 1,3-cyclopentadiene and the alkali metal hydride is performed under the conditions described above, the 1,3-cyclopentadiene is anionized with the result that an alkali metal cyclopentadienylide is formed. The yield is generally 80 to 100%, and in many cases, at least 85%.

When, after the completion of the above reaction, any excess alkali metal hydride is removed by filtration, the product is obtained in the form of a colorless to red solution. The solution containing the product is colored red when oxygen is included in the reaction vessel but generally has the color of yellow to orange.

The disubstituted or trisubstituted alkali metal cyclopentadienylide can be isolated in solid form by heating the solution having been obtained by the filtration to evaporate the solvent therefrom.

The thus obtained product is the alkali metal cyclopentadienylide represented by the following general formula [II]. Specifically, the alkali metal cyclopentadienylide represented by the following general formula [II-a] is obtained from the disubstituted 1,3-cyclopentadiene represented by the above general formula [I-a]. The alkali metal cyclopentadienylide represented by the following general formula [II-b] is obtained from the trisubstituted 1,3-cyclopentadiene represented by the above general formula [I-b].

In the general formula:

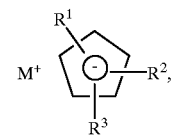

[II]

$R^1$, $R^2$ and $R^3$ are as defined above with respect to the general formula [I]; and $M^+$ is an alkali metal ion.

In the general formula:

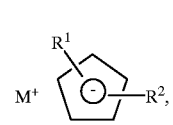

[II-a]

$R^1$ and $R^2$ are as defined above with respect to the general formula [I-a]; and $M^+$ is an alkali metal ion.

In the general formula:

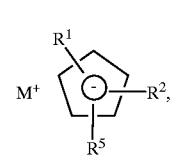

[II-b]

$R^1$, $R^2$ and $R^5$ are as defined above with respect to the general formula [I-b]; and $M^+$ is an alkali metal ion.

The alkali metal cyclopentadienylide represented by the general formula [II-a] is, for example, an alkali metal salt of any of the 1,3-cyclopentadienes listed as examples of the disubstituted 1,3-cyclopentadienes represented by the general formula [I-a] (alkali metal salt of disubstituted cyclopentadienyl anion).

Of the compounds represented by the above general formula [II-a], a 1,3-disubstituted compound wherein $M^+$ is a sodium ion, $R^1$ is an alkyl group having 1 to 6 carbon atoms, preferably an alkyl group having 1 to 4 carbon atoms, and $R^2$ is a methyl group is a novel substance which can specifically be represented by the following general formula [II-c]:

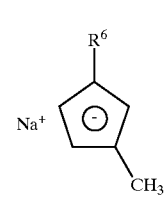

[II-c]

wherein $R^6$ is an alkyl group having 1 to 6 carbon atoms. Examples of $R^6$ include those listed for $R^1$ above.

Further, the alkali metal cyclopentadienylide represented by the general formula [II-b] is, for example, an alkali metal salt of any of the 1,3-cyclopentadienes listed as examples of the trisubstituted 1,3-cyclopentadienes represented by the general formula [I-b] (alkali metal salt of trisubstituted cyclopentadienyl anion).

These alkali metal cyclopentadienylides are generally stored in the form of a solution and such a solution per se can be used in a subsequent reaction, for example, reaction for introducing a cyclopentadienyl in a carbonyl compound or an alkyl halide.

Now, the process for producing a dihalobis(η-substituted-cyclopentadienyl)zirconium according to the present invention will be described.

In accordance with the present invention, a dihalobis(η-substituted-cyclopentadienyl)zirconium can be synthesized by the reaction between the alkali metal cyclopentadienylide produced by the above process according to the present invention and a zirconium halide. The zirconium halide includes halides of zirconium (II), (III) and (IV). Preferred are zirconium (IV) halides, and particularly preferred is zirconium tetrachloride.

This reaction can generally be performed in a molar ratio of alkali metal cyclopentadienylide to zirconium halide of from 0.5 to 5.0, preferably, from 1.4 to 2.6.

In this reaction, a solvent which is inert in the reaction can be used. In the present invention, it is preferred to employ a process in which the alkali metal cyclopentadienylide is dissolved in the above ether solvent in advance and the resultant solution is mixed with a suspension of the zirconium halide.

As the solvent for suspending the zirconium halide, there can be used a solvent which is inert in the reaction, such as hexane, heptane or toluene, and also the above-mentioned ether solvent.

The above reaction is preferably performed in an atmosphere of inert gas. This reaction is generally performed at −40 to 80° C., preferably, 0 to 70° C. for a period of 10 min to 10 hr, preferably, 0.5 to 5 hr.

The dihalobis(η-substituted-cyclopentadienyl)zirconium produced by the above process is represented by the following general formula [III] and is useful as an olefin polymerization catalyst, an acetylene carbometallizing reagent, a starting material for the synthesis of a monohydride homologue and a vulcanizing agent for a silicone material and a rubber.

In the general formula:

[III]

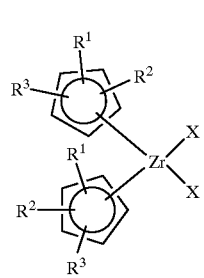

each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms; and $R^3$ is a hydrogen atom or an alkyl group having 1 to 3 carbon atoms. Examples of $R^1$, $R^2$ and $R^3$ are those described for the above general formula [I], respectively. X is a halogen atom, and examples thereof include fluorine, chlorine, bromine and iodine. Particularly preferred is chlorine.

The dihalobis(η-substituted-cyclopentadienyl)zirconium represented by the above general formula [III] is, for example, one produced by the reaction between any of the alkali metal cyclopentadienylides listed as examples of the alkali metal cyclopentadienylides of the general formulae [II-a] and [II-b] and a zirconium halide. Preferred products are the corresponding zirconium dichloride compounds.

Effect of the Invention

The process for producing an alkali metal cyclopentadienylide according to the present invention enables performing the reaction between the disubstituted or trisubstituted 1,3-cyclopentadiene and the alkali metal hydride at an easily controllable temperature such as room temperature to about 150° C., preferably, 50 to 100° C. and further enables obtaining the alkali metal cyclopentadienylide with high yield. Such unexpectedly advantageous industrial effects have first been achieved by the use of the alkali metal hydride.

Moreover, the process for producing a dihalobis(η-substituted-cyclopentadienyl)zirconium according to the present invention enables producing the dihalobis(η-substituted-cyclopentadienyl)zirconium with high yield.

EXAMPLE

The present invention will now be illustrated in greater detail with reference to the following Examples, which in no way limit the scope of the invention.

Example 1

Synthesis of sodium 1,3-dimethylcyclopentadienylide

A mixture of 4.84 g (51.5 mmol) of 1,3-dimethylcyclopentadiene, 2.47 g (net 61.8 mmol in terms of NaH) of a mineral oil dispersion of 60% sodium hydride and 36 ml of tetrahydrofuran (THF) was heated in a nitrogen atmosphere and refluxed for 20 hr. The reaction mixture gradually colored and, 20 hr later, an orange to red suspension was obtained. The reaction mixture was allowed to cool, and any excess sodium hydride was separated by filtration. Thus, 38.8 g of an orange to red transparent solution was obtained. This solution was subjected to a potentiometric titration using a 0.1 N aqueous hydrochloric acid solution. As a result, it was found that the concentration of sodium 1,3-dimethylcyclopentadienylide was 1.19 mmol/g, the yield thereof being 90%.

THF-$d_8$ was added to this solution, and the product was analyzed by $^1$H-NMR. As a result, it was found to be sodium 1,3-dimethylcyclopentadienylide.

THF was removed from the transparent solution by the use of a vacuum pump. Thus, 5.32 g of sodium salt of 1,3-dimethylcyclopentadienyl anion (sodium 1,3-dimethylcyclopentadienylide) was obtained in the form of a dark-red solid.

Example 2

Synthesis of dichlorobis(1,3-dimethylcyclopentadienyl)zirconium 41.3 g of the THF solution of sodium 1,3-dimethyl-cyclopentadienylide obtained by the synthesis in Example 1, the solution temperature set at 0 to 7° C., was dropwise added to a toluene (20 g) suspension of 5.83 g (25 mmol) of zirconium tetrachloride and the mixture was agitated at the same temperature for 10 min and then at 25° C. for 1 hr. The mixture was further agitated for 2 hr under reflux.

Thereafter, the resultant solution was cooled to room temperature, and solid matter was separated by filtration. The filtrate was concentrated to obtain 12.97 g of a light-brown oil.

15 g of heptane was added to this light-brown oil, separated precipitate was removed by filtration, and the filtrate was further concentrated to obtain 7.85 g of a light-yellow crude crystal. This crude crystal was dissolved in heptane and recrystallized at 0° C. Thus, 5.66 g (yield: 65%) of white needle crystal of dichlorobis(1,3-dimethylcyclopentadienyl)zirconium was obtained.

Example 3

Synthesis of sodium 3-butyl-1-methylcyclopentadienylide

A mixture of 7.01 g (51.5 mmol) of 3-butyl-1-methylcyclopentadiene, 2.06 g (net 51.8 mmol in terms of NaH) of a mineral oil dispersion of 60% sodium hydride and 36 ml of tetrahydrofuran (THF) was heated in a nitrogen atmosphere and refluxed for 23 hr. The reaction mixture gradually colored and, 23 hr later, an orange to red suspension was obtained. The reaction mixture was allowed to cool, and any excess sodium hydride was separated by filtration. Thus, 15.2 g of an orange to red transparent solution was obtained. This solution was subjected to a potentiometric titration using a 0.1 N aqueous hydrochloric acid solution. As a result, it was found that the concentration of sodium 3-butyl-1-methylcyclopentadienylide was 3.29 mmol/g, the yield thereof being 97%.

THF-$d_8$ was added to this solution, and the product was analyzed by $^1$H-NMR. As a result, it was found to be sodium 3-butyl-1-methylcyclopentadienylide. δ value:

0.91 ppm (3H, m, CH$_2$CH$_2$CH$_2$C$\underline{H}_3$),
1.32 ppm (2H, m, CH$_2$CH$_2$C$\underline{H}_2$CH$_3$),
1.42 ppm (2H, m, CH$_2$C$\underline{H}_2$CH$_2$CH$_3$),
2.05 ppm (3H, s, CH$_3$),
2.38 ppm (2H, m, C$\underline{H}_2$CH$_2$CH$_2$CH$_3$), and
5.20 ppm (3H, m,

).

THF was removed from the transparent solution by the use of a vacuum pump. Thus, 7.50 g of sodium salt of 3-butyl-1-methylcyclopentadienyl anion (sodium 3-butyl-1-methylcyclopentadienylide) was obtained in the form of a dark-red solid.

Example 4

Synthesis of dichlorobis(3-butyl-1-methylcyclopentadienyl)zirconium 15.2 g of the THF solution of sodium 3-butyl-1-methylcyclopentadienylide obtained by the synthesis in Example 3, the solution temperature set at 0 to 7° C., was dropwise added to a toluene (20 g) suspension of 5.83 g (25 mmol) of zirconium tetrachloride and the mixture was agitated at the same temperature for 10 min, and then at 25° C. for 1 hr. The mixture was further agitated for 2 hr under reflux.

Thereafter, the resultant solution was cooled to room temperature, and solid matter was separated by filtration. The filtrate was concentrated to obtain 17.35 g of a light-brown oil.

20 g of heptane was added to this light-brown oil, separated precipitate was removed by filtration, and the filtrate was further concentrated to obtain 11.25 g of a light-yellow crude crystal (melting point: 47 to 51° C.). This crude crystal was dissolved in heptane and recrystallized at 0° C. Thus, 8.11 g (yield: 75%) of a white needle crystal was obtained. This white needle crystal was the desired dichlorobis(3-butyl-1-methylcyclopentadienyl)zirconium having a melting point of 50 to 55° C.

Comparative Example 1

Synthesis of lithium 3-butyl-1-methylcyclopentadienylide using n-butyl lithium

A 15% hexane solution of 26.3 g (61.3 mmol) of n-butyl lithium was dropwise added to a tetrahydrofuran (THF, 7.01 g) solution of 7.01 g (51.5 mmol) of 3-butyl-1-methylcyclopentadiene in a nitrogen atmosphere at 0° C. After the dropwise addition, the mixture was agitated at the same temperature for 1 hr, and then at 25° C. for 2 hr. 25 mmol of toluene as an internal standard was added to the reaction mixture, followed by sampling into a NMR tube. THF-$d_8$ was added to the sample and the product was analyzed by $^1$H-NMR. As a result, it was found that lithium 3-butyl-1-methylcyclopentadienylide was produced in a yield of 82%.

Comparative Example 2

Synthesis of lithium 3-butyl-1-methylcyclopentadienylide using n-butyl lithium

The reaction and work up procedures as in Comparative Example 1 were followed, except that the dropwise addition of the hexane solution of n-butyl lithium was carried out at 28 to 36° C. and the mixture after the dropwise addition was refluxed (70° C.) for 6 hr. As a result of analysis buy $^1$H-NMR, it was found that lithium 3-butyl-1-methylcyclopentadienylide was produced in a yield of only 26%.

Comparative Example 3

Synthesis of sodium 3-butyl-1-methylcyclopentadienylide using sodium

A mixture of 7.01 g (51.5 mmol) of 3-butyl-1-methylcyclopentadiene, 1.20 g (52.2 mmol) of a sodium dispersion and 7.01 g of tetrahydrofuran (THF) was agitated in a nitrogen atmosphere at 25° C. for 23 hr, but there was no sign that any reaction was took place. To make sure, 26 mmol of toluene as an internal standard was added to the reaction mixture, followed by sampling into a NMR tube. THF-$d_8$ was added to the sample and the product was analyzed by $^1$H-NMR. As a result, it was found, however, that no sodium 3-butyl-1-methylcyclopentadienylide was produced.

What is claimed is:

1. A process for producing an alkali metal cyclopentadienylide, comprising reacting at a temperature from 50° C. to 150° C. in a solvent an alkali metal hydride with a disubstituted or trisubstituted 1,3-cyclopentadiene represented by the general formula:

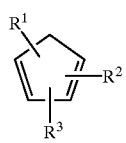

[I]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms; and $R^3$ is a hydrogen atom or an alkyl group having 1 to 3 carbon atoms, thereby obtaining an alkali metal cyclopentadienylide represented by the general formula:

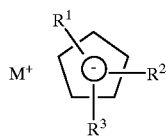

[II]

wherein $R^1$, $R^2$ and $R^3$ are as defined above with respect to the general formula (I); and $M^+$ is an alkali metal ion.

2. The process as claimed in claim 1, wherein an alkali metal hydride is reacted in an ether solvent with a disubstituted 1,3-cyclopentadiene represented by the general formula:

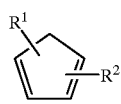

[I-a]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms, thereby obtaining an alkali metal cyclopentadienylide represented by the general formula:

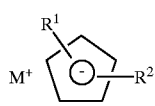

[II-a]

wherein $R^1$ and $R^2$ are as defined above with respect to the general formula [I-a]; and $M^+$ is an alkali metal ion.

3. The process as claimed in claim 2, wherein the disubstituted 1,3-cyclopentadiene is a 1,3-cyclopentadiene having alkyl substituents at its 1- and 3-positions.

4. The process as claimed in claim 3, wherein the disubstituted 1,3-cyclopentadiene is a disubstituted 1,3-cyclopentadiene having a methyl group at its 3-position, represented by the formula:

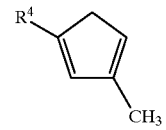

wherein $R^4$ is an alkyl group having 1 to 8 carbon atoms, an aryl group having 6 to 10 carbon atoms or an aralkyl group having 7 to 9 carbon atoms.

5. The process as claimed in claim 1, wherein an alkali metal hydride is reacted in an ether solvent with a trisubstituted 13-cyclopentadiene represented by the general formula:

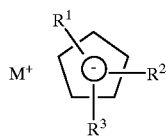

[I-b]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms; and $R^5$ is an alkyl group having 1 to 3 carbon atoms, thereby obtaining an alkali metal cyclopentadienylide represented by the general formula:

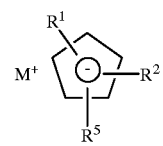

[II-b]

wherein $R^1$, $R^2$ and $R^5$ are as defined above with respect to the general formula [I-b]; and $M^+$ is an alkali metal ion.

6. The process as claimed in claim 1, wherein the disubstituted or trisubstituted 1,3-cyclopentadiene and the alkali metal hydride are reacted at a temperature of 50 to 100° C.

7. The process as claimed in claim 1, wherein the disubstituted or trisubstituted 1,3-cyclopentadiene and the alkali metal hydride are reacted in a nitrogen gas atmosphere.

8. The process as claimed in claim 1, wherein a saturated cyclic ether having a 5- or 6-membered ring is used as the solvent.

9. The process as claimed in claim 1, wherein the solvent is used in an amount of 50 to 200 parts by weight based on 100 parts by weight of the cyclopentadiene.

10. A sodium salt compound of a 1,3-disubstituted cyclopentadienyl anion represented by the general formula:

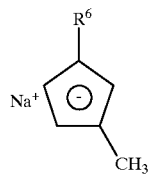
[II-c]

wherein $R^6$ is an alkyl group having 1 to 6 carbon atoms.

11. A process for producing a dihalobis(η-substituted-cyclopentadienyl)zirconium, comprising reacting a zirconium halide with the alkali metal cyclopentadienylide produced by the process of claim 1, thereby obtaining a dihalobis(η-substituted-cyclopentadienyl)zirconium represented by the general formula:

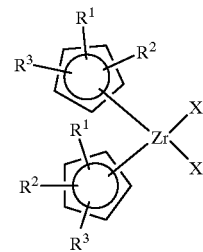
[III]

wherein each of $R^1$ and $R^2$ is independently an alkyl group having 1 to 8 carbon atoms, an aryl group having 6 to 10 carbon atoms, an alkenyl group having 2 to 8 carbon atoms or an aralkyl group having 7 to 9 carbon atoms;

$R^3$ is a hydrogen atom or an alkyl group having 1 to 3 carbon atoms; and

X is a halogen atom.

* * * * *